(12) United States Patent
Thompson et al.

(10) Patent No.: US 8,734,902 B2
(45) Date of Patent: May 27, 2014

(54) PRECURSORS AND METHODS FOR THE ATOMIC LAYER DEPOSITION OF MANGANESE

(75) Inventors: David Thompson, San Jose, CA (US); Jeffrey W. Anthis, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 13/415,358

(22) Filed: Mar. 8, 2012

(65) Prior Publication Data

US 2012/0231164 A1 Sep. 13, 2012

Related U.S. Application Data

(60) Provisional application No. 61/451,767, filed on Mar. 11, 2011.

(51) Int. Cl.
 *C23C 16/00* (2006.01)
(52) U.S. Cl.
 USPC .......... 427/252; 427/250; 427/248.1
(58) Field of Classification Search
 USPC ........... 427/252, 250, 248.1; 556/46; 548/101
 See application file for complete search history.

(56) References Cited

U.S. PATENT DOCUMENTS

| 7,737,290 B2 | 6/2010 | Gordon et al. | |
|---|---|---|---|
| 2008/0026576 A1 | 1/2008 | Shenai-Khatkhate et al. | |
| 2009/0291208 A1* | 11/2009 | Gordon et al. | 427/252 |
| 2010/0092667 A1 | 4/2010 | Gordon et al. | |

OTHER PUBLICATIONS

Schmidt et al. First row transistion metal complexes of sterically-hindered amidinates. J Chem Soc, Dalton Trans, 2002 pp. 3545-3461.*
PCT International Search Report & Written Opinion in PCT/US2012/028421, mailed Oct. 19, 2012, 11 pgs.
Lim, Booyong S. et al., "Synthesis and Characterization of Volatile, Thermally Stable, Reactive Transition Metal Amidinates", *Inorg. Chem., 42* 2003, 7951-7958.
Schmidt, Joseph A. et al., "First-row transition metal complexes of sterically-hindered amidinates", *J. Chem. Soc., Dalton Trans.* 2002, 3454-3461.
Bermejo, Maria-Jose et al., "Dynamic behaviour of octahedral complexes of manganese(I). X-Ray crystal structure of *fac*-[Mn($\eta^1$-1,8-naphthyridine)-$\eta_2$-1,8-naphthyridine)(CO)$_3$]ClO$_4$ CH$_2$Cl$_2$", *Journal of Organometallic Chemistry, 463* 1993, 143-150.
Gibson, Dorothy H. et al., "Synthesis of Allyl Complexes of Iron, Manganese and Molybdenum by Phase Transfer Catalysis", *Journal of Organometallic Chemistry, 172* 1979, C7-C12.
McClellan, W. R. et al., "n-Allyl Derivatives of Transition Metals", *E.I. du Pont de Nemours and Company, Inc.,* Wilmington, DE Apr. 5, 1961, 1601-1607.
PCT IPRP & Written Opinion in PCT/US2012/028421, dated Sep. 17, 2013, 7 pgs.

* cited by examiner

*Primary Examiner* — Kelly M Gambetta
(74) *Attorney, Agent, or Firm* — Servilla Whitney LLC

(57) ABSTRACT

Methods and precursors are provided for deposition of elemental manganese films on surfaces using metal coordination complexes comprising an eta-3-bound monoanionic four-electron donor ligands selected from amidinate, mixed ene-amido and allyl, or eta-2 bound amidinate ligand. The ligands are selected from amidinate, ene-amido, and allyl.

20 Claims, 2 Drawing Sheets

PRECURSORS AND METHODS FOR THE ATOMIC LAYER DEPOSITION OF MANGANESE

CROSS REFERENCE PARAGRAPH

This application claims priority to U.S. Provisional Application No. 61/451,767, filed Mar. 11, 2011, the contents of which are hereby incorporated by reference in their entirety.

TECHNICAL FIELD

The present invention relates generally to methods of depositing thin films of elemental metal and to metal coordination complexes useful in such methods. In particular, the invention relates to the use of coordination complexes of manganese in the atomic layer deposition process.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures. One method for deposition of thin films with atomic layer control and conformal deposition is atomic layer deposition (ALD), which employs sequential, self-limiting surface reactions to form layers of precise thickness controlled at the Angstrom or monolayer level. Most ALD processes are based on binary reaction sequences which deposit a binary compound film. Each of the two surface reactions occurs sequentially, and because they are self-limiting, a thin film can be deposited with atomic level control. Because the surface reactions are sequential, the two gas phase reactants are not in contact, and possible gas phase reactions that may form and deposit particles are limited. The self-limiting nature of the surface reactions also allows the reaction to be driven to completion during every reaction cycle, resulting in films that are continuous and pinhole-free.

ALD has been used to deposit metals and metal compounds on substrate surfaces. $Al_2O_3$ deposition is an example of a typical ALD process illustrating the sequential and self-limiting reactions characteristic of ALD. $Al_2O_3$ ALD conventionally uses trimethylaluminum (TMA, often referred to as reaction "A" or the "A" precursor) and $H_2O$ (often referred to as the "B" reaction or the "B" precursor). In step A of the binary reaction, hydroxyl surface species react with vapor phase TMA to produce surface-bound $AlOAl(CH_3)_2$ and $CH_4$ in the gas phase. This reaction is self-limited by the number of reactive sites on the surface. In step B of the binary reaction, $AlCH_3$ of the surface-bound compound reacts with vapor phase $H_2O$ to produce AlOH bound to the surface and $CH_4$ in the gas phase. This reaction is self-limited by the finite number of available reactive sites on surface-bound $AlOAl(CH_3)_2$. Subsequent cycles of A and B, purging gas phase reaction products and unreacted vapor phase precursors between reactions and between reaction cycles, produces $Al_2O_3$ growth in an essentially linear fashion to obtain the desired film thickness.

While perfectly saturated monolayers are often desired, this goal is very difficult to achieve in practice. The typical approach to further ALD development has been to determine whether or not currently available chemistries are suitable for ALD. Prior art processes for ALD have been most effective for deposition of metal oxide and metal nitride films. Although a few processes have been developed that are effective for deposition of elemental ruthenium and other late transition metals, in general ALD processes for deposition of pure metal have not been sufficiently successful to be adopted commercially. There is a need for new deposition chemistries that are commercially viable, particularly in the area of elemental metal films. The present invention addresses this problem by providing novel chemistries which are specifically designed and optimized to take advantage of the atomic layer deposition process. In fact, before the present invention, there were no known commercially acceptable atomic layer deposition precursors that are capable of producing thin manganese films. There are known methods of depositing thin manganese metal films via physical deposition methods in back end of the line processes. However, the thin metal films deposited this way have been shown to migrate to $SiO_2$ interfaces. This forms manganese oxide, which acts as a barrier layer and prevents copper diffusion.

SUMMARY

Embodiments of the invention provide methods for producing thin films of elemental manganese on a substrate using metal coordination complexes as source material, wherein the metal coordination complex is based on manganese (I) with a $Mn(CO)_4$ core and an eta-3-bound monoanionic four-electron donor ligand selected from amidinate, mixed ene-amido and allyl, or eta-2 bound amidinate ligand. The thin films may be produced using atomic layer deposition (ALD) processes, including plasma enhanced atomic layer deposition (PEALD) processes.

One aspect of the invention relates to a metal coordination complex having a formula represented by $XMn(CO)_4$, wherein X is an amidinate or mixed ene-amido ligand, and has a structure represented by:

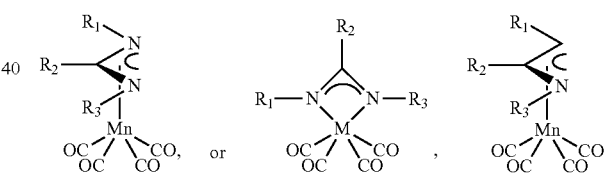

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen. In one embodiment, $R_1$ and $R_3$ are the same. In other embodiments, $R_2$ is an electron withdrawing group or an electron donating group.

In another embodiment, a method of depositing manganese metal by atomic layer deposition is provided, the method comprising contacting a surface of a substrate with a vapor phase metal coordination complex having the formula $XMn(CO)_4$, wherein X is an eta-3-bound monoanionic 4-electron donor ligand selected from allyl, and mixed ene-amido, such that a layer is formed on the surface comprising the metal coordination complex bound to the surface by the manganese; and contacting the bound metal complex with a reducing gas such that an exchange reaction occurs between the bound metal coordination complex and the reducing gas, thereby dissociating the bound metal complex and producing a first layer of elemental manganese on the surface of the substrate. One embodiment of the invention relates to this method, wherein the manganese is bound to the ligand at three contiguous atoms comprising carbon and/or nitrogen. In one or more embodiments, the metal coordination complex has a structure represented by:

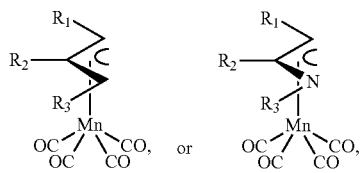

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen. In further embodiments, $R_1$ and $R_3$ may be the same, and/or $R_2$ is an electron withdrawing or donating group.

A third aspect of the invention relates to method of depositing manganese metal by atomic layer deposition, the method comprising, contacting a surface of a substrate with a vapor phase metal coordination complex having the formula $XMn(CO)_4$, wherein X is an amidinate ligand having a structure represented by:

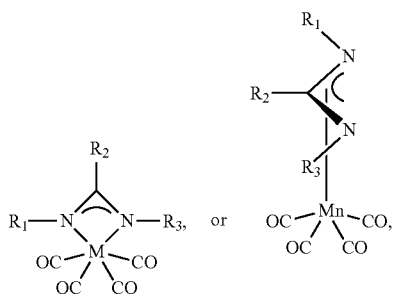

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen, such that a layer is formed on the surface comprising the metal coordination complex bound to the surface by the manganese; and contacting the bound metal complex with a reducing gas such that an exchange reaction occurs between the bound metal coordination complex and the reducing gas, thereby dissociating the bound metal complex and producing a first layer of elemental manganese on the surface of the substrate. In certain embodiments $R_1$ and $R_3$ are the same, $R_2$ is an electron withdrawing group, and/or $R_2$ is an electron donating group. This aspect may also further comprise purging excess unreacted vapor phase metal complex with an inert gas prior to addition of the reducing gas.

In one or more embodiments of the methods described herein, the method further comprises contacting the first layer of elemental manganese on the substrate surface with the vapor phrase metal coordination complex such that an exchange reaction occurs between the metal complex and the first layer of elemental metal, thereby partially dissociating the metal complex and producing a second layer on the surface comprising the partially dissociated metal complex bound to the first elemental manganese layer by manganese; and contacting the bound metal complex of the second layer with a reducing gas such that an exchange reaction occurs between the bound metal complex and the reducing gas, thereby dissociating the bound metal complex and producing a second layer of elemental manganese on the surface of the substrate.

Another aspect of the invention relates to a method of forming manganese metal on a substrate surface, the method comprising: during an atomic layer deposition process, exposing a substrate to a vapor phase metal coordination complex having the formula $XMn(CO)_4$, wherein X is an eta-3-bound monoanionic 4-electron donor ligand selected from amidinate, mixed ene-amido and allyl, or eta-2 bound amidinate ligand, such that a layer is formed on the surface comprising the metal coordination complex bound to the surface by the manganese; during an atomic layer deposition process, exposing the substrate having bound metal complex with a reducing gas such that an exchange reaction occurs between the bound metal coordination complex and the reducing gas, thereby dissociating the bound metal complex and producing a first layer of elemental manganese on the surface of the substrate; and sequentially repeating the atomic layer deposition process and the treatment.

Yet another aspect of the invention relates to a method of forming manganese on a substrate surface, comprising: (a) disposing a substrate within a process chamber; (b) flowing a vapor phase metal coordination complex having the formula $XMn(CO)_4$, wherein X is an eta-3-bound monoanionic 4-electron donor ligand selected from amidinate, mixed ene-amido and allyl or eta-2 bound amidinate, such that a layer is formed on the surface comprising the metal coordination complex bound to the surface by the manganese; (c) purging the process chamber; (d) flowing a reducing gas such that an exchange reaction occurs between the bound metal coordination complex and the reducing gas, thereby dissociating the bound metal complex and producing a first layer of elemental manganese on the surface of the substrate; (e) purging the process chamber; repeating (a) through (e).

DETAILED DESCRIPTION

Figure 1:
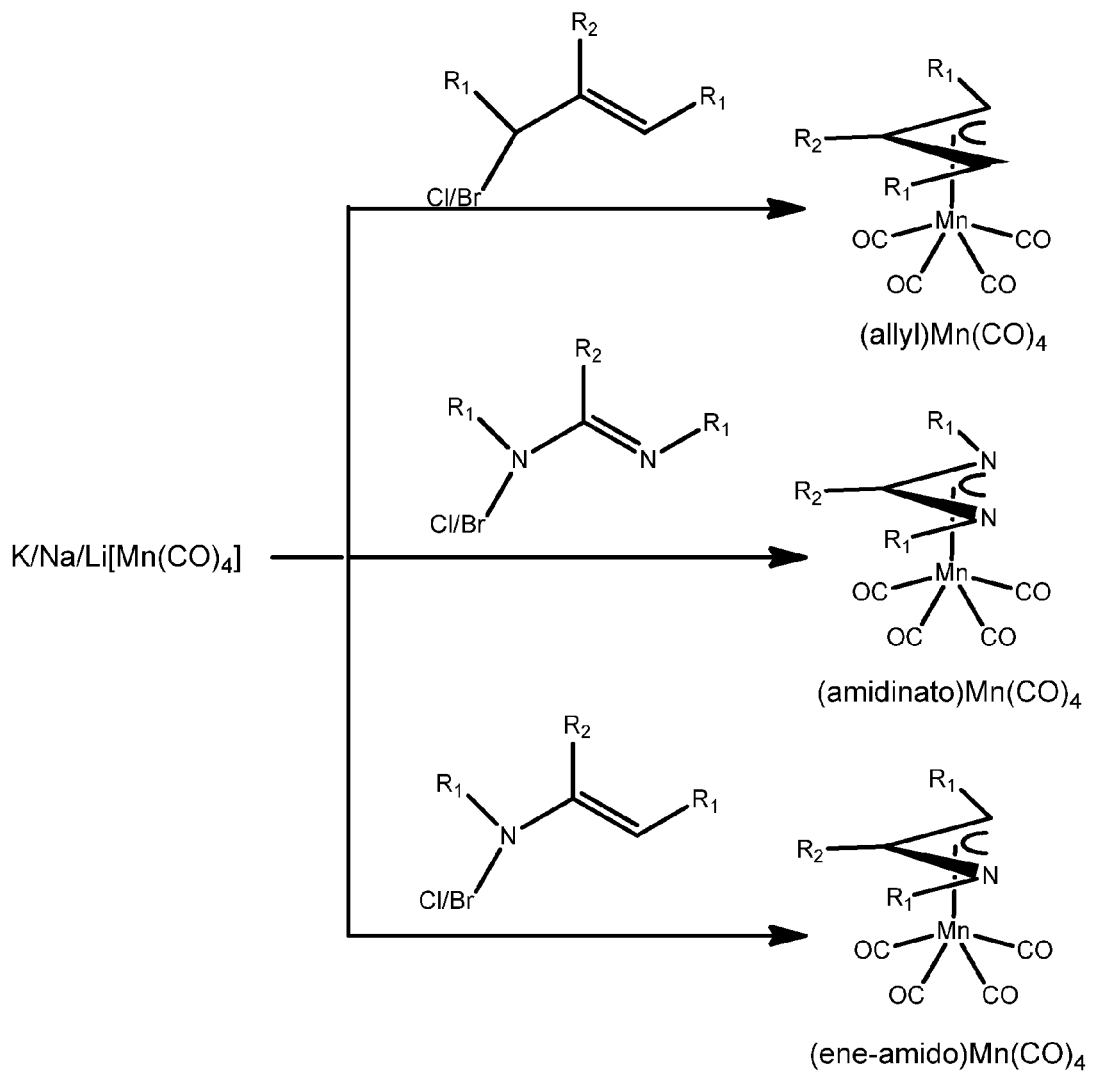
FIG. 1 is a schematic showing possible methods for synthesis of coordination complexes with a $Mn(CO)_4$ core and an eta-3 bound monoanionic four-electron donor ligand selected from amidinato, mixed ene-amido, and allyl, or eta-2 amidinato.

Before describing several exemplary embodiments of the invention, it is to be understood that the invention is not limited to the details of construction or process steps set forth in the following description. The invention is capable of other embodiments and of being practiced or being carried out in various ways. It is also to be understood that the complexes and ligands of the present invention may be illustrated herein using structural formulas which have a particular stereochemistry. These illustrations are intended as examples only and are not to be construed as limiting the disclosed structure to any particular stereochemistry. Rather, the illustrated structures are intended to encompass all such complexes and ligands having the indicated chemical formula.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

The term "metal coordination complex" as used herein is used interchangeably with "metal complex" and "coordination complex," and includes structures that consist of a central metal atom bonded to one or more ligands. As will be discussed in more detail below, the metal complexes of the invention comprise of ligands eta-3 or eta-2 bound to metals.

In one embodiment of the invention, the ligand useful for forming the metal coordination complex may be a member of one of three groups of structurally related compounds, represented by the formula $XMn(CO)_4$, wherein X is an eta-3 bound monoanionic four electron donor ligand selected from amidinate, mixed ene-amido and allyl, or eta-2 bound amidinate ligand. A first such group of ligands is eta-3 allyl. As an example, the first group of ligands may be represented by formula (I):

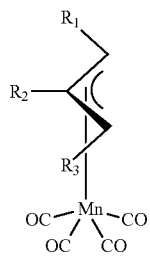

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen. In another embodiment, $R_1$ and $R_3$ are the same substituent.

A second such group of ligands is amidinate, which may be either eta-2 or eta-3. As an example, the second group of ligands may be represented by formula (IIa):

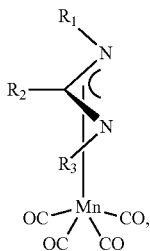

or formula (IIb):

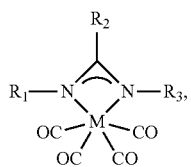

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen. In another embodiment, $R_1$ and $R_3$ are the same substituent.

A third such group of ligands is mixed ene-amido. As an example, the third group of ligands may be represented by formula (III):

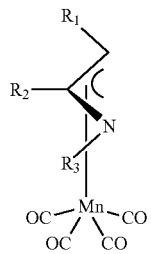

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen. In another embodiment, $R_1$ and $R_3$ are the same substituent.

In all above ligands formulae (I)-(III), the R group substituents may be selected to control characteristics of the metal coordination complex. $R_1$ and $R_3$ may be selected to tune the sterics of the precursor. Sterics should be selected such that the precursor does not become too bulky, and the vapor pressure will drop to an unusable level for vapor deposition. Additionally, $R_2$ may be selected to tune the electronics of the precursor. In one embodiment, $R_2$ is selected to be an electron withdrawing group. In another embodiment, $R_2$ is selected to be an electron donating group.

The synthesis of the precursors with the three groups of ligands is shown in FIG. 1. Na, K or Li $Mn(CO)_4$ is reacted with an organic chloride or bromide. The organic chloride or bromide can be an allyl, amidinato or mixed ene-amido, depending on the desired ligand. Although the structure shown for the metal coordination complex comprising an amidinato ligand is eta-3, it is possible the ligand will be eta-2 bound to the Mn atom. Additionally, the organic chloride or bromide has the desired R substituents. In one or more embodiments of the invention, the process for preparing thin films of elemental metal is an ALD process.

Accordingly, one aspect of the invention relates to a method of depositing manganese metal by atomic layer deposition, the method comprising: contacting a surface of a substrate with a vapor phase metal coordination complex having the formula $XMn(CO)_4$, wherein X is an eta-3-bound monoanionic 4-electron donor ligand selected from amidinate, mixed ene-amido and allyl, or eta-2 bound amidinate ligand, such that a layer is formed on the surface comprising the metal coordination complex bound to the surface by the manganese; and contacting the bound metal complex with a reducing gas such that an exchange reaction occurs between the bound metal coordination complex and the reducing gas, thereby dissociating the bound metal complex and producing a first layer of elemental manganese on the surface of the substrate. In further specific embodiment, the manganese is bound to the ligand at three contiguous atoms comprising carbon and/or nitrogen. In yet a further specific embodiment, this method uses a metal coordination complex having a structure represented by formula (I), (IIa), (IIb) or (III).

Figure 2:
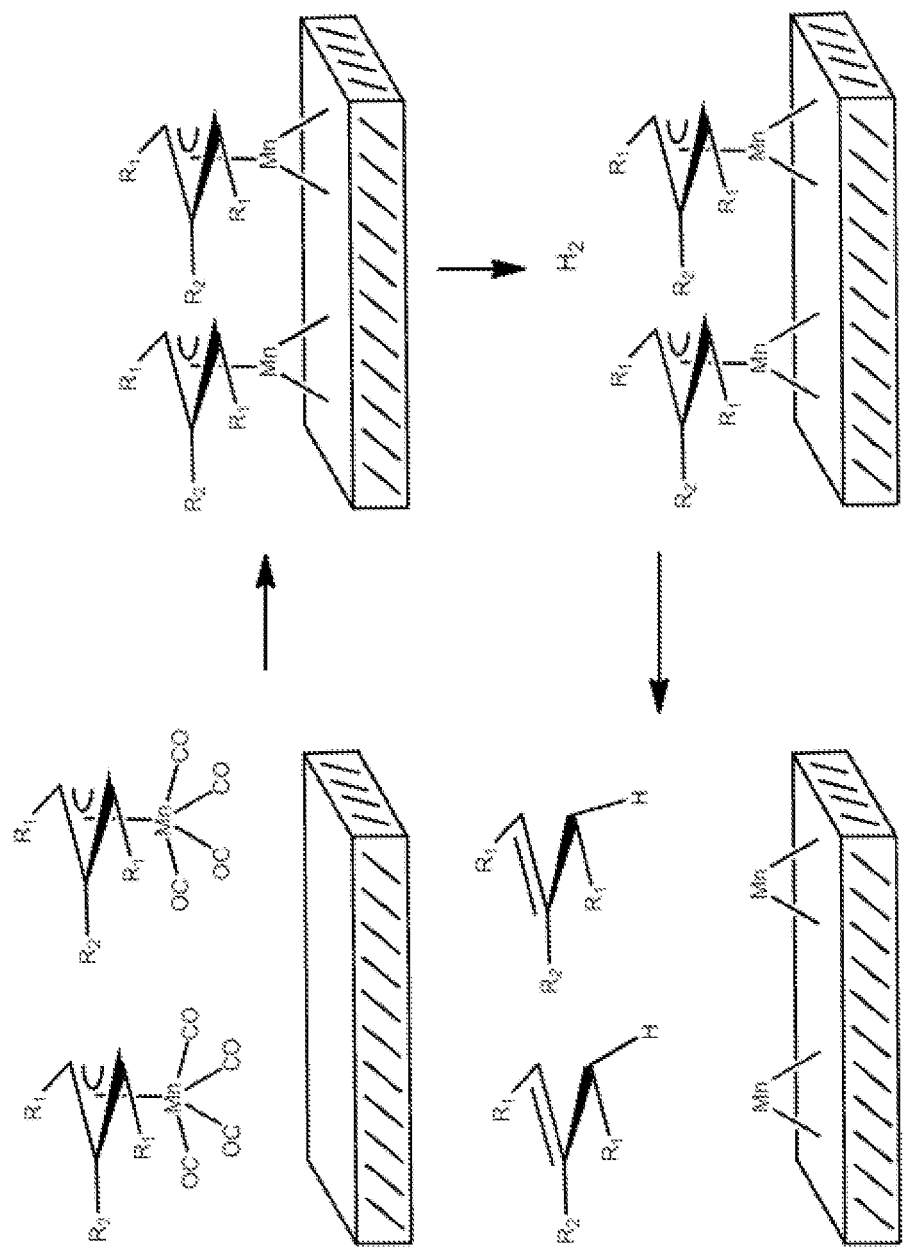
FIG. 2 an illustration of an ALD process using a representative metal coordination complex according to the invention.

In the illustrative example of such a process shown in FIG. 2, the metal coordination complex used is represented by formula (I). As illustrated, the metal coordination complex is vaporized, optionally in a mixture with an inert carrier gas, and flowed in the vapor phase to a substrate within a deposition chamber (not shown). The substrate has a surface that is appropriate for adsorption of the metal coordination complex to the surface via the metal ion when the carbonyl ligands dissociate from the complex, exposing an active site for bonding with the surface. In one embodiment, the substrate used is a semiconductor wafer. The CO ligands dissociate due to their relatively weak interaction with the Mn metal center while the allyl ligand requires a reducing gas to be removed from the metal center. In this example the surface for adsorption may be bare metal. The surface is exposed to the metal coordination complex for sufficient time to permit adsorption of the complex in a layer on the surface. A reducing gas is then flowed into the deposition chamber to reduce the bond(s) in the ligand, releasing the allyl ligand from the metal center and leaving an atomic layer of elemental metal on the substrate. In one embodiment, the reducing gas used is hydrogen. In another embodiment, the process also includes purging excess unreacted vapor phase metal complex with an inert gas prior to addition of the reducing gas. In yet another embodiment, the vapor phase metal complex is in a mixture with an inert gas In another embodiment, a method of forming manganese metal on a substrate surface comprises: during an atomic layer deposition process, exposing a substrate to a vapor phase metal coordination complex having the formula XMn(CO)$_4$, wherein X is an eta-3-bound monoanionic 4-electron donor ligand selected from amidinate, mixed ene-amido and allyl, or eta-2 bound amidinate ligand, such that a layer is formed on the surface comprising the metal coordination complex bound to the surface by the manganese; during an atomic layer deposition process, exposing the substrate having bound metal complex with a reducing gas such that an exchange reaction occurs between the bound metal coordination complex and the reducing gas, thereby dissociating the bound metal complex and producing a first layer of elemental manganese on the surface of the substrate; and sequentially repeating the atomic layer deposition process and the treatment. In a further embodiment, this process uses a metal coordination complex having a structure represented by formula (I), (IIa), (IIb) and/or (III).

Another embodiment of the invention relates to a method of forming manganese on a substrate surface, comprising: (a) disposing a substrate within a process chamber; (b) flowing a vapor phase metal coordination complex having the formula XMn(CO)$_4$, wherein X is an eta-3-bound monoanionic 4-electron donor ligand selected from amidinate, mixed ene-amido and allyl, or eta-2 bound amidinate ligand, such that a layer is formed on the surface comprising the metal coordination complex bound to the surface by the manganese; (c) purging the process chamber; (d) flowing a reducing gas such that an exchange reaction occurs between the bound metal coordination complex and the reducing gas, thereby dissociating the bound metal complex and producing a first layer of elemental manganese on the surface of the substrate; (e) purging the process chamber; repeating (a) through (e).

Optionally, a second atomic layer of elemental metal may be formed added on the first atomic layer by repeating the process of the reaction cycle. Hydrogen remaining from the preceding reduction reaction is purged from the deposition chamber using an inert gas and a metal coordination complex in vapor phase is again flowed into the chamber into contact with the metal film on the substrate surface. An exchange reaction occurs between the metal coordination complex in the vapor phase and hydrogen atoms on the metal of the first atomic layer. This displaces one of the ligands from the vapor phase metal coordination complex and leaves the metal atom of the metal coordination complex bound to the metal atom of the first atomic layer. The reaction time, temperature and pressure are selected to create a metal-surface interaction and form a layer on the surface of the substrate. Unreacted vapor phase metal coordination complex and released ligand are purged from the deposition chamber using an insert gas. A reducing gas is flowed into the deposition chamber to reduce the bond(s) between the metal and any remaining ligand(s), releasing the remaining ligand(s) from the metal center and producing a second atomic layer of elemental metal on the first atomic layer of elemental metal.

In one embodiment, a second layer of manganese may be added by contacting the first layer of elemental manganese on the substrate surface with the vapor phrase metal coordination complex such that an exchange reaction occurs between the metal complex and the first layer of elemental metal, thereby partially dissociating the metal complex and producing a second layer on the surface comprising the partially dissociated metal complex bound to the first elemental manganese layer by manganese; and contacting the bound metal complex of the second layer with a reducing gas such that an exchange reaction occurs between the bound metal complex and the reducing gas, thereby dissociating the bound metal complex and producing a second layer of elemental manganese on the surface of the substrate Additional repetitions of the deposition cycle may be used to build a layer of elemental metal of the desired thickness.

In an alternative aspect of the ALD deposition methods of the invention the substrate has a surface that is activated for reaction with the metal coordination complex to form a first layer on the substrate. A metal coordination complex according to the invention is vaporized and flowed in the vapor phase to a substrate within a deposition chamber. The reaction between the allyl, amidinate or mixed ene-amido metal coordination complex and the surface may occur by an exchange reaction in which hydrogen atoms on the surface displace eta-3 bound monoanionic ligands selected from amidinate, mixed ene-amido and allyl, or eta-2 bound amidinate ligand, from the complex or one of the carbonyl ligands bound to the metal. The metal atom becomes bound to the surface. The reaction time, temperature and pressure are selected to create a metal-surface interaction and achieve a layer on the surface of the substrate. The first layer comprises the metal bound to the surface and coordinated with at least one ligand. Following formation of the first monolayer, precursor gas containing unreacted eta-3 bound monoanionic 4 electron donor ligand selected from amidinate, mixed ene-amido and allyl, or eta-2 bound amidinate ligand, metal coordination complex and released ligand are purged from the deposition chamber using an inert gas. A reducing gas is then flowed into the deposition chamber to reduce the remaining bond(s) between the metal and the ligand(s) of the coordination complex, releasing the remaining ligand(s) from the metal center and leaving an atomic layer of elemental metal on the substrate.

As in the adsorption ALD process discussed above, a second atomic layer of elemental metal may optionally be formed on the first atomic layer by repeating the process of the reaction cycle. Hydrogen remaining from the preceding reduction reaction is purged from the deposition chamber using an inert gas and a metal coordination complex in vapor phase is again flowed into the chamber into contact with the metal film on the substrate surface. An exchange reaction occurs between the metal coordination complex in the vapor phase and hydrogen atoms on the metal of the first atomic layer. This displaces one of the ligands from the vapor phase metal coordination complex, reducing the displaced ligand and leaving the metal atom of the metal coordination complex bound to the metal atom of the first atomic layer. The reaction time, temperature and pressure are selected to achieve a uniform layer on the surface of the substrate. Unreacted vapor phase metal coordination complex and released ligand are purged from the deposition chamber using an insert gas. A reducing gas is flowed into the deposition chamber to reduce the bond(s) between the metal and any remaining ligand(s), releasing the remaining ligand(s) from the metal center and producing a second uniform atomic layer of elemental metal on the first atomic layer of elemental metal.

Additional repetitions of the deposition cycle may be used to build a layer of elemental manganese of the desired thickness.

The substrate for deposition of the elemental thin layer films may be any substrate suitable for conformal film coating in an ALD or CVD process. Such substrates include silicon, silica or coated silicon, metal, metal oxide and metal nitride. In one aspect of the invention, the substrate is a semiconductor substrate.

The reaction conditions for the ALD reaction will be selected based on the properties of the selected ligand containing an eta-3 bound monoanionic four-electron donor ligand selected from amidinate, mixed ene-amido and allyl, or eta-2 bound amidinate ligand metal coordination complex. The deposition can be carried out at atmospheric pressure but is more commonly carried out at a reduced pressure. The vapor pressure of the metal coordination complex should be low enough to be practical in such applications. The substrate temperature should be high enough to keep the bonds between the metal atoms at the surface intact and to prevent thermal decomposition of gaseous reactants. However, the substrate temperature should also be high enough to keep the source materials (i.e., the reactants) in the gaseous phase and to provide sufficient activation energy for the surface reaction. The appropriate temperature depends on the specific metal coordination complex used and the pressure. The properties of a specific metal coordination complex for use in the ALD deposition methods of the invention can be evaluated using methods known in the art, allowing selection of appropriate temperature and pressure for the reaction. In general, lower molecular weight and the presence of functional groups that increase the rotational entropy of the ligand sphere result in a melting point that yields liquids at typical delivery temperatures and increased vapor pressure.

An optimized metal coordination complex with a $Mn(CO)_4$ core and eta-3 bound monoanionic four electron donor ligand selected from amidinate, mixed ene-amido and allyl, or eta-2 bound amidinate ligand, for use in the deposition methods of the invention will have all of the requirements for sufficient vapor pressure, sufficient thermal stability at the selected substrate temperature and sufficient reactivity to produce a self-limiting reaction on the surface of the substrate without unwanted impurities in the thin film or condensation. Sufficient vapor pressure ensures that molecules of the source compound are present at the substrate surface in sufficient concentration to enable a complete self-saturating reaction. Sufficient thermal stability ensures that the source compound will not be subject to the thermal decomposition which produces impurities in the thin film.

Any metal coordination complex based on a manganese(I) with a $Mn(CO)_4$ core and an eta-3 bound monoanionic four electron donor ligand selected from amidinate, mixed ene-amido and allyl, or eta-2 bound amidinate ligand, including but not limited to complexes represented by formula (I), formula (IIa), formula (IIb), and formula (III), and having suitable vapor pressure properties may be used in the thin layer film deposition methods of the invention.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A metal coordination complex having a structure represented by:

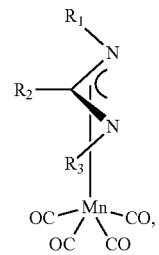

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen.

2. The metal coordination complex of claim 1, wherein $R_1$ and $R_3$ are the same.

3. The metal coordination complex of claim 1, wherein $R_2$ is an electron withdrawing group.

4. The metal coordination complex of claim 1, wherein $R_2$ is an electron donating group.

5. A method of depositing manganese metal by atomic layer deposition, the method comprising:

contacting a surface of a substrate with a vapor phase metal coordination complex having the formula $XMn(CO)_4$, wherein X is an eta-3-bound monoanionic 4-electron donor ligand selected from allyl and ene-amido, such that a layer is formed on the surface comprising the metal coordination complex bound to the surface by the manganese; and contacting the bound metal complex with a reducing gas such that an exchange reaction occurs between the bound metal coordination complex and the reducing gas, thereby dissociating the bound metal complex and producing a first layer of elemental manganese on the surface of the substrate.

6. The method of claim 5, wherein the manganese is bound to the ligand at three contiguous atoms comprising carbon, nitrogen and combinations thereof.

7. The method of claim 5, wherein the metal coordination complex has a structure represented by

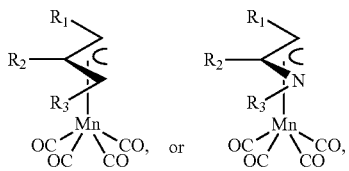

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen.

8. The method of claim 7, wherein $R_1$ and $R_3$ are the same.

9. The method of claim 7, wherein $R_2$ is an electron withdrawing group.

10. The method of claim 7, wherein $R_2$ is an electron donating group.

11. The method of claim 7, wherein the substrate is a semiconductor wafer.

12. The method of claim 5, wherein the reducing gas is hydrogen.

13. The method of claim 5, further comprising purging excess unreacted vapor phase metal complex with an inert gas prior to addition of the reducing gas.

14. The method of claim 5, the method further comprising:
   a. contacting the first layer of elemental manganese on the substrate surface with the vapor phrase metal coordination complex such that an exchange reaction occurs between the metal complex and the first layer of elemental metal, thereby partially dissociating the metal complex and producing a second layer on the surface comprising the partially dissociated metal complex bound to the first elemental manganese layer by manganese; and
   b. contacting the bound metal complex of the second layer with a reducing gas such that an exchange reaction occurs between the bound metal complex and the reducing gas, thereby dissociating the bound metal complex and producing a second layer of elemental manganese on the surface of the substrate.

15. A method of depositing manganese metal by atomic layer deposition, the method comprising:
   contacting a surface of a substrate with a vapor phase metal coordination complex having the formula $XMn(CO)_4$, wherein X is an amidinate ligand having a structure represented by:

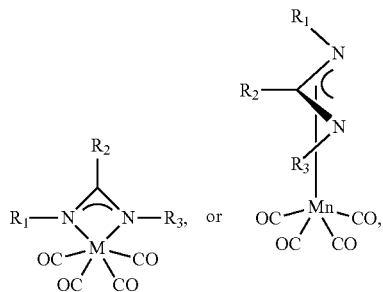

wherein $R_1$ and $R_3$ are each independently hydrogen, $C_{1-6}$ alkyl, aryl, acyl, aldehyde, keto, $C_{2-4}$ alkenyl, alkynyl, nitrogen or $CF_3$, and $R_2$ is hydrogen, $C_{1-6}$ alkyl, acyl, aldehyde, keto, $C_{2-4}$ alkenyl, nitrogen, $CF_3$, oxygen or halogen, such that a layer is formed on the surface comprising the metal coordination complex bound to the surface by the manganese; and
   contacting the bound metal complex with a reducing gas such that an exchange reaction occurs between the bound metal coordination complex and the reducing gas, thereby dissociating the bound metal complex and producing a first layer of elemental manganese on the surface of the substrate.

16. The method of claim 15, wherein $R_1$ and $R_3$ are the same.

17. The method of claim 15, wherein $R_2$ is an electron withdrawing group.

18. The method of claim 15, wherein $R_2$ is an electron donating group.

19. The method of claim 15, further comprising purging excess unreacted vapor phase metal complex with an inert gas prior to addition of the reducing gas.

20. The method of claim 15, the method further comprising:
   a. contacting the first layer of elemental manganese on the substrate surface with the vapor phrase metal coordination complex such that an exchange reaction occurs between the metal complex and the first layer of elemental metal, thereby partially dissociating the metal complex and producing a second layer on the surface comprising the partially dissociated metal complex bound to the first elemental manganese layer by manganese; and
   b. contacting the bound metal complex of the second layer with a reducing gas such that an exchange reaction occurs between the bound metal complex and the reducing gas, thereby dissociating the bound metal complex and producing a second layer of elemental manganese on the surface of the substrate.

\* \* \* \* \*

UNITED STATES PATENT AND TRADEMARK OFFICE
CERTIFICATE OF CORRECTION

| | |
|---|---|
| PATENT NO. | : 8,734,902 B2 |
| APPLICATION NO. | : 13/415358 |
| DATED | : May 27, 2014 |
| INVENTOR(S) | : David Thompson and Jeffrey W. Anthis |

It is certified that error appears in the above-identified patent and that said Letters Patent is hereby corrected as shown below:

In the Claims,

Claim 15, Column 12, line 11, in the first structure, change M to read -- Mn --.

Signed and Sealed this
Twenty-fourth Day of February, 2015

Michelle K. Lee
*Deputy Director of the United States Patent and Trademark Office*